US011304973B2

(12) United States Patent
Moeller et al.

(10) Patent No.: US 11,304,973 B2
(45) Date of Patent: Apr. 19, 2022

(54) BOTULINUM TOXIN AND COLLOIDAL SILVER PARTICLES

(71) Applicants: Keith William Moeller, Highland, UT (US); Andrew J. M. Willoughby, Vancouver (CA)

(72) Inventors: Keith William Moeller, Highland, UT (US); Andrew J. M. Willoughby, Vancouver (CA)

(73) Assignees: American Silver, LLC, American Fork, UT (US); Dr. Andrew Willoughby Inc., Vancouver (CA)

( * ) Notice: Subject to any disclaimer, the term of this patent is extended or adjusted under 35 U.S.C. 154(b) by 0 days.

(21) Appl. No.: 15/415,808

(22) Filed: Jan. 25, 2017

(65) Prior Publication Data

US 2017/0196946 A1 Jul. 13, 2017

Related U.S. Application Data

(63) Continuation-in-part of application No. PCT/US2015/047601, filed on Aug. 28, 2015.

(60) Provisional application No. 62/044,926, filed on Sep. 2, 2014.

(51) Int. Cl.

| | |
|---|---|
| ***A61K 38/48*** | (2006.01) |
| ***A61K 33/38*** | (2006.01) |
| ***A61K 8/04*** | (2006.01) |
| ***A61K 8/19*** | (2006.01) |
| ***A61K 8/66*** | (2006.01) |
| ***A61K 9/00*** | (2006.01) |
| ***A61K 9/10*** | (2006.01) |
| ***A61Q 19/08*** | (2006.01) |
| ***A61K 47/02*** | (2006.01) |
| ***A61K 8/64*** | (2006.01) |
| ***A61K 9/19*** | (2006.01) |

(52) U.S. Cl.

CPC .............. *A61K 33/38* (2013.01); *A61K 8/042* (2013.01); *A61K 8/044* (2013.01); *A61K 8/19* (2013.01); *A61K 8/64* (2013.01); *A61K 8/66* (2013.01); *A61K 9/0019* (2013.01); *A61K 9/10* (2013.01); *A61K 9/19* (2013.01); *A61K 38/4893* (2013.01); *A61K 47/02* (2013.01); *A61Q 19/08* (2013.01); *A61K 2800/41* (2013.01); *A61K 2800/413* (2013.01); *A61K 2800/882* (2013.01); *A61K 2800/91* (2013.01)

(58) Field of Classification Search

CPC ........ A61K 38/4893; A61K 8/66; A61K 8/19; A61K 33/38; A61K 8/044; A61K 9/10; A61K 9/0019; A61K 2800/41; A61Q 19/08

See application file for complete search history.

(56) References Cited

U.S. PATENT DOCUMENTS

| | | | | |
|---|---|---|---|---|
| 6,214,299 B1 | 4/2001 | Holladay et al. | | |
| 6,447,787 B1 | 9/2002 | Gassner | | |
| 6,720,006 B2 | 4/2004 | Hanke | | |
| 6,743,348 B2 | 6/2004 | Holladay et al. | | |
| 7,135,195 B2 | 11/2006 | Holladay et al. | | |
| 7,211,261 B1 * | 5/2007 | Moyer | A61K 8/64 | 424/236.1 |
| 8,318,181 B2 | 11/2012 | Edelson et al. | | |
| 8,535,728 B2 | 9/2013 | Holladay et al. | | |
| 8,876,020 B2 | 11/2014 | Holladay et al. | | |
| 2007/0059255 A1 | 3/2007 | Tichy | | |
| 2007/0190174 A1 | 8/2007 | Holladay | | |
| 2010/0055138 A1 * | 3/2010 | Margulies | A61K 8/02 | 424/401 |
| 2010/0159016 A1 * | 6/2010 | Kim | A61K 33/00 | 424/489 |
| 2010/0168023 A1 * | 7/2010 | Ruegg | A61K 8/64 | 514/8.9 |
| 2010/0187091 A1 | 7/2010 | Pierce et al. | | |
| 2011/0052636 A1 * | 3/2011 | Gaxiola | A61K 38/4893 | 424/239.1 |
| 2011/0262556 A1 * | 10/2011 | Holladay | A01N 59/16 | 424/616 |
| 2011/0293681 A1 | 12/2011 | Berlin | | |
| 2012/0064136 A1 | 3/2012 | Baker et al. | | |
| 2014/0086900 A1 | 3/2014 | Jung et al. | | |
| 2014/0099342 A1 | 4/2014 | Edelson et al. | | |
| 2017/0281678 A1 | 12/2017 | Moeller et al. | | |

FOREIGN PATENT DOCUMENTS

| | | |
|---|---|---|
| WO | 20000015245 A1 | 3/2000 |
| WO | 2008079898 A1 | 7/2008 |
| WO | 2009009143 | 1/2009 |
| WO | 2011154126 | 12/2011 |
| WO | 2012048854 | 4/2012 |
| WO | 2013107687 | 7/2013 |
| WO | 2013151671 | 10/2013 |
| WO | 2015153377 | 10/2015 |
| WO | 2016036618 | 3/2016 |

OTHER PUBLICATIONS

International Search Report and Written Opinion for PCT/US2015/047601 dated Dec. 4, 2015.

European Extended Search Report dated Apr. 3, 2018, for Application No. 15839012.0.

Singapore Examination Report dated May 30, 2018, for Application No. 11201701619T.

Thenganatt, Mary Ann et al., "Treatment of Dystonia", Neurotherapeutics, Elsevier Inc., US, vol. 11, No. 1, Oct. 19, 2013, pp. 139-152.

* cited by examiner

*Primary Examiner* — Doan T Phan

(74) *Attorney, Agent, or Firm* — BioMed IP

(57) ABSTRACT

Botulinum toxin is combined with colloidal silver particles to provide improved compositions for use in medical and cosmetic treatments.

4 Claims, No Drawings

BOTULINUM TOXIN AND COLLOIDAL SILVER PARTICLES

CROSS-REFERENCE TO RELATED APPLICATION

This application is a continuation-in-part of International Application No. PCT/US2015/047601, filed Aug. 28, 2015, which application claims the benefit under 35 U.S.C. § 119(e) of U.S. Provisional Patent Application No. 62/044,926 filed Sep. 2, 2014, each application is incorporated herein by reference in its entirety.

FIELD OF THE INVENTION

The present invention relates generally to botulinum toxin in combination with colloidal silver particles for medical and cosmetic purposes.

BACKGROUND

In the 1950's, scientists discovered that botulinum toxin can reduce muscle spasms. In the 1960's and 1970's, studies were performed to explore botulinum toxin as a treatment for strabismus (crossed eyes). In 1989, Allergan Inc. Irvine, Calif., USA introduced BOTOX®, the first botulinum toxin approved by the FDA to treat blepharospasm (eyelid spasms) and strabismus. In 2000, the FDA approved BOTOX® therapy for cervical dystonia to reduce the severity of abnormal head position and neck pain. In 2002, the FDA approved BOTOX® Cosmetic (onabotulinumtoxin A), the same formulation as BOTOX®, with dosing specific to moderate to severe frown lines between the brow. In 2004, the FDA approved BOTOX® for severe underarm sweating when topical medicines don't work well enough. Several other preparations of botulinum toxin are now commercially available and sold under various tradenames.

Unfortunately, therapeutic and cosmetic administration of botulinum toxin provides a treatment but not a cure for various conditions. Accordingly, repeated administration is necessary in order to maintain beneficial results. For example, for cosmetic applications, such as to remove frown lines, BOTOX® is typically administered every 3-6 months in order to achieve and maintain a wrinkle-free (or reduced) appearance. The body may degrade botulinum toxin and thereby destroy the biological efficacy of the material.

All of the subject matter discussed in the Background section is not necessarily prior art and should not be assumed to be prior art merely as a result of its discussion in the Background section. Along these lines, any recognition of problems in the prior art discussed in the Background section or associated with such subject matter should not be treated as prior art unless expressly stated to be prior art. Instead, the discussion of any subject matter in the Background section should be treated as part of the inventor's approach to the particular problem, which in and of itself may also be inventive.

SUMMARY

The present disclosure provides the combination of colloidal silver particles and botulinum toxin. In exemplary aspects, the present disclosure provides compositions, kits, and methods of use that include both colloidal silver particles and botulinum toxin. For instance, in one aspect the present disclosure provides compositions comprising botulinum toxic and colloidal silver particles, including the following exemplary embodiments:

1) A composition comprising botulinum toxin (BTX), colloidal silver particles and water.
2) The composition of embodiment 1 wherein the BTX is botulinum type A neurotoxin.
3) The composition of embodiment 1 wherein the BTX is botulinum type B neurotoxin.
4) The composition of embodiment 1 comprising 100-600 units of BTX.
5) The composition of embodiment 1 comprising a concentration of colloidal silver of 1 to 100 ppm.
6) The composition of embodiment 1 wherein the colloidal silver is characterized by particle size, and more than 50% of the colloidal silver particles have a maximum dimension of less than 0.015 micrometers.
7) The composition of embodiment 6 wherein at least 90% of the colloidal silver particles have diameters between 0.005 micrometers and 0.015 micrometers.
8) The composition of embodiment 1 wherein the colloidal silver particles comprise metal silver of formula Ag(0) and ionic silver of a formula selected from Ag(I), Ag(II), and Ag(III).
9) The composition of embodiment 1 having a total concentration of silver of between about 5 and 40 parts per million, wherein said silver is in the form of a stable and colorless colloidal suspension of silver particles having an interior of metallic silver and an exterior surface of ionic silver oxide, wherein at least 75% of the silver particles have diameters between 0.005 micrometers and 0.015 micrometers.

In another aspect, the present disclosure provides a kit that comprises both botulinum toxin and colloidal silver particles in separate containers. For instance, the present disclosure provides the following exemplary embodiments:

10) A kit comprising a container comprising botulinum toxin (BTX) and a container comprising colloidal silver particles and water.
11) The kit of embodiment 10 further comprising a needle and syringe suitable for transferring the colloidal silver particles to the container of BTX.

In another aspect, the present disclosure provides methods of using botulinum toxin (BTX) and colloidal silver particles. For instance, the present disclosure provides the following exemplary embodiments:

12) A cosmetic treatment comprising administering botulinum toxin (BTX), colloidal silver particles and water to a subject in need thereof.
13) A medical treatment comprising administering botulinum toxin (BTX), colloidal silver particles and water to a subject in need thereof.

More specifically for embodiment 13), the present disclosure provides treatment for a variety of medical conditions, where that treatment includes administration of BTX and silver particles in combination with water, e.g., $Ag_4O_4$-containing silver particles as described in more detail herein. The following exemplary medical conditions may be treated by the BTX/Ag (BB) composition as disclosed herein, and thus the present disclosure provides methods that include administration of an effective amount of a pharmaceutical composition comprising BTX/Ag to a patient that has the medical condition and thus is in needed of the treatment. The medical conditions include headaches, TMJC, clenching and grinding of the jaw, strabismus, blepherospasm, hyperhidrosis, urinary incontinence, and premature ejaculation. The administration of a BTX/Ag composition of the present disclosure achieves a reduction in the symptoms of the medical condition, e.g., a headache of less painful severity or duration.

The details of one or more aspects and embodiments are set forth in the description below. The features illustrated or described in connection with one exemplary embodiment may be combined with the features of other embodiments. Other features, objects and advantages will be apparent from the description, and the claims.

DETAILED DESCRIPTION OF THE INVENTION

Briefly stated the present invention provides the combination of colloidal silver particles and botulinum toxin, including kits, compositions and methods of use thereof.

The following abbreviations having the indicated meaning may be used herein: ACS: American College of Surgeons; ABL: American Biotech Labs, LLC; AE: Adverse event; ASA: American Society of Anesthesiologists Physical Status Classification System; ASA I: A normal healthy patient; healthy, non-smoking, no or minimal alcohol use; ASA II: A patient with mild systemic disease; mild diseases only without substantive functional limitations. Examples include (but not limited to): current smoker, social alcohol drinker, pregnancy, obesity (30<BMI<40), well-controlled DM/HTN, mild lung disease; ATP: Adult Treatment Panel; APP: a self-contained program or piece of software designed to fulfill a particular purpose; an application, especially as downloaded by a user to a mobile device; BID: Twice daily; CDSBC: College of Dental Surgeons of British Columbia; CEC: Clinical Events Committee; CRF: Case report forms; CT: Computed tomography; DMC: Data Monitoring Committee; DRF: Discrepancy resolution form; EMG: is an electrodiagnostic medicine technique for evaluating and recording the electrical activity produced by skeletal muscles; GCP: Good Clinical Practice; GMP: Good Manufacturing Practices; ICH: International Conference on Harmonization; IP: Investigational product; IRB/EC: Institutional Review Board/Ethics Committee; ITT: Intent-to-treat; XXXCTW: Interactive voice response system; MedDRA: Medical Dictionary for Regulatory Activities; MRI: Magnetic resonance imaging; OD: Once daily; PSU: Partial shipment unit; SAE: Serious adverse event; TMJD: Temporo Mandibular Joint Dysfunction; ULN: Upper limit of normal range; USP: United States Pharmacoepia; VTI: VeraSIL Therapeutics USA Inc.; WHO: World Health Organization; WOC: Withdrawal of consent.

Colloidal Silver Particles

The terms "colloidal silver particles" or "colloidal silver" refers to particles which in whole or in part comprise silver, where the particles are colloidally suspended in an aqueous medium. The total amount of colloidal silver particles in a composition is typically between 1 and 100 ppm. In optional embodiments, the content of colloidal silver particles in the composition is about 30±5 ppm, or 25±5 ppm, or 20±5 ppm, or 15±5 ppm, or 10±5 ppm. As the particles become smaller, a given concentration of particles will represent a larger number of particles. In addition, the total surface area for a given particle concentration will increase. Therefore, particle size and range of particle size may further characterize the compositions of the present invention. In further embodiments, the present disclosure provides that more than 50% of the particles have a maximum dimension less than 0.015 micrometers; or that more than 75% of the particles have a maximum dimension less than 0.015 micrometers; or that more than 90% of the particles have a maximum dimension less than 0.02 micrometers; or that more than 75% of the particles have a minimum dimension greater than 0.005 micrometers; or that more than 90% of the particles have a minimum dimension greater than 0.005 micrometers.

The particles may optionally be characterized in terms of valence of the silver. In one embodiment, the silver particles include both silver in the zero-valent state represented as [Ag(0)], i.e., metallic silver, and a coating of silver in an ionic oxidation state selected from Ag(I), Ag(II), and Ag(III). Optionally, the particles may include silver oxide, e.g., AgO. For example, in one embodiment the particles comprise Ag(0) and AgO, where AgO is present as a coating on the particles. In one embodiment, the silver oxide in the particles may be at least partially in the form of $Ag_4O_4$, i.e., silver II oxide. In a molecule of this material two of the silver atoms are in the 1+ state (silver I) while the other two silver molecules are in the 3+ state (silver III). Under certain conditions these molecules can give rise to silver atoms in the 2+ (silver II) state. Thus, the present disclosure provides silver particles comprising metallic silver and silver oxide, the silver oxide being selected from AgO and $Ag_4O_4$.

Within optional embodiments of the invention these particles can range in size from 1 to 100 nanometers, or from 1 to 10 nanometers, or from 5 to 7 nanometers. When the particles have a size on the nanometer scale, i.e., a diameter of from 1 to 100 nanometers, those particles may be referred to as nanometallic silver (NMS), and when in a solution may be referred to as NMSS (nanometallic silver solution) and when in a hydrosol may be referred to as NMSH (nanometallic silver hydrosol). Moreover, within preferred embodiments the particles are surrounded by a multivalent silver oxide coating comprised of $Ag_4O_4$ molecules.

Exemplary aqueous compositions comprising colloidal silver particles are described in, and may be prepared by techniques disclosed in U.S. Pat. Nos. 6,214,299; 6,743,348; 7,135,195; and 8,535,728 as well as U.S Publication No. 2011/0262556. For example, the preparation of a composition comprising colloidal silver particles may utilize an electrochemical cell comprising electrodes. The process comprises the steps of: (a) placing a silver electrode in contact with a quantity of high purity water; (b) conveying electrical current through the silver electrode to thereby separate particles of silver from said silver electrode in a manner sufficient to cause production of suspended silver particles within the water; and (c) agitating the water during said production of suspended silver particles to thereby disperse the silver particles into a more uniform concentration within said water such that a higher quantity of colloidal silver particles can be produced per batch.

As another example, the preparation of a composition comprising colloidal silver particles may comprise the steps of: (a) establishing an electrical circuit comprising a current source, and a first conductor electrically connected to said current source and a second conductor electrically connected to said current source, wherein said first conductor is disposed spaced apart from said second conductor, and wherein at least one of the conductors is made of elemental silver; (b) closing the circuit by placing the first conductor and the second conductor in communication with a fluidic resistor; (c) operating the current source to supply alternating current simultaneously to the first conductor and the second conductor such that voltage is increasing and decreasing within the first and second conductors in alternating tandem to thereby cause silver particles to separate from the first electrode and enter the fluidic resistor and become disposed in suspension within said fluidic resistor; and (d) selectively adjusting the electrodes by moving them toward the fluidic resistor to compensate for decrease in electrode length due to gradual separation of silver particles therefrom to thereby prevent arcing from occurring between the electrodes and said fluidic resistor.

Other suitable colloidal silver particles and their preparation are described in, e.g., PCT Publication No. WO 2009/009143 and US Publication No. 2010/0187091. Colloidal silver is available commercially from, e.g., American Biotech Labs (ABL) of Alpine, Utah, USA. For example, ABL has 510(k) premarket approval (number K151185 for AGRX® Wound Wash Antibacterial Silver Skin And Wound Cleanser (Rx) And AGX® Wound Wash Skin And Wound Cleanser (OTC), which may be used as a source of colloidal silver according to the present disclosure. The AGRX® solution contains silver at a concentration of 10 ppm in addition to deionized water.

In one embodiment the colloidal silver is provided by a product known as AGRX® from ABL as mentioned above. AGRX® exerts three effects of silver (antimicrobial, pro-healing, and anti-inflammatory effects) that positively affect wound healing, which, though likely having separate mechanisms of action, are difficult to separate when assessing changes in wound healing. As to the antimicrobial properties: AGRX® rapidly kills microbes by blocking the cell respiration pathway. The efficacy of microbe killing is based not only on the amount of silver ion present, but likely also the presence of other silver radicals generated by a silver-releasing product. AGRX® releases less silver than other silver products, but the nanocrystalline structure in AGRX® allows for a greater surface area for silver release over a longer period of time. The rate and degree of microbial killing is significantly faster with AGRX® than other silver products. A possible explanation is that silver and a number of potent silver radicals are released from the silver nanocrystals on the membrane. These radicals may have more potent antimicrobial properties than silver alone. As to the pro-healing effects, AGRX® therapy has been associated with increased re-epithelialization of non-infected partial-thickness acute wounds. Therefore, in addition to antibacterial properties, there appears to be a pro-healing property to silver. The mechanism of the pro-healing properties has yet to be defined. In contrast, silver salts and complexes, especially silver nitrate and silver sulfadiazine, appear to impede re-epithelialization. As to the anti-inflammatory properties of silver, defining anti-inflammatory properties of silver, which can improve healing, is difficult because of silver's potent antimicrobial activity. However, silver does decrease surface zinc, a cofactor for metalloproteinase activity (MMP) activity. The decrease in MMP activity would be advantageous in a burn wound or a chronic wound; an excess of MMP activity may retard healing. Silver blocks MMP activity in an in-vitro model. Silver has also been reported to increase wound surface calcium. Calcium, in turn, has been reported to increase re-epithelialization rate. Since excess inflammation retards healing, an anti-inflammatory effect would be of benefit. In summary, the multiple actions of silver in AGRX® formulation explains both its activity against multiple microbial pathogens and why AGRX® is the silver-based wound wash with the most proven clinical applications, and may be used to provide silver for the BTX/silver compositions and uses of the present disclosure.

In one embodiment, the colloidal silver particles are stable in essentially pure water without surfactants, etc. Additionally, or in another embodiment, the solution of colloidal silver particles is essentially colorless. The colloidal silver may be present in a hydrosol.

BTX

As used herein, the term "BTX" is used to generally to refer to botulinum toxin. Botulinum toxin is a neurotoxin protein naturally produced by various bacteria, e.g., *Clostridium botulinum* as described below. At least eight different serotypes of BTX are recognized, and they are commonly designated as A, B, C1, C2, D, E, F, and G. Exemplary sources of BTX are *C. argentinense, C. baratii, C. botulinum*, and *C. butyricum*. In one embodiment, the BTX is BTX-A. In one embodiment, the BTX is BTX-B. The term BTX as used herein includes pieces, portions and fragments of the neurotoxic protein that retain neurotoxin activity (e.g., the ability to relax muscle). The light chain and/or the heavy chain of the neurotoxin are examples of fragments of the neurotoxin. In addition to fragments, BTX also refers to complexes that include the neurotoxin. Isolated botulinum toxin itself has a molecular weight of about 150 kD, and homo-complexes of botulinum, which are within the scope of BTX, may have molecular weights of, e.g., 300, 600, and 900 kD. The BTX may in a pure state, e.g., free from other proteins, or it may be in combination with or in complex with other proteins. A purified neurotoxin may be greater than 95% pure, and preferably is greater than 99% pure. The BTX may be isolated from a bacteria, including the bacteria mentioned above, or it may be obtained through chemical synthesis, or it may be produced recombinantly (i.e., in a host cell or organism other than C. botulinum), as well as by other means. Thus, the BTX of the present disclosure is not limited to being obtained from any particular source.

Each of BTX-A and BTX-B are approved for human use by the FDA for several indications and are commercially available from several sources. For example, BOTOX® is available from Allergan Inc. Irvine, Calif., USA. DYSPORT® is available from Valeant Pharmaceuticals Int'l. Inc., Laval, Quebec, Canada. NEUROBLOC® and MYOBLOC® are both available from Solstice Neurosciences Inc. Malvern, Pa., USA. XEOMIN® is available from Merz Pharma GmbH & Co. KGaA, Frankfurt am Main, Germany.

BTX may be obtained from commercial sources as a lyophilized powder (see, e.g., U.S. Publication No. US 2014/0086900). It may be combined with water or saline at physiological pH at a suitable concentration for its intended cosmetic or medical use. BTX concentrations are generally expressed in terms of mouse units. One unit is equal to the amount of BTX that kills 50% of a group of 18- to 22-g Swiss Webster mice when injected intraperitoneally. Different BTX materials will have a different weight of BTX per unit. Indeed, different preparations of a BTX material may have a different weight of BTX per unit. BOTOX® injections of less than 100 units are usually used for cosmetic purposes and of less than 300-600 units for other purposes. The amount of aqueous solution added to the lyophilized BTX will depend on the intended purpose. 100 units commonly are reconstituted in 1-10 mL of diluent. As an example, for oculoplastic purposes 1-mL dilution per 100 units of BTX may be used. As another example, for dermatology and plastic surgery purposes, a range from 1-4 mL per 100 units may be used. As another example, 100 unit of BTX may be diluted with about 1 mL of aqueous composition comprising silver nanoparticles at a concentration of about 1 to about 50 ppm to provide a composition that may be injected into a patient to treat wrinkles such as frown lines. The aqueous phase may be gently injected into the vial of powdered BTX via syringe. The vials are typically provided by the manufacturer having a negative pressure, so that fluid is pulled into the vial upon injection. After reconstitution, the aqueous BTX composition is preferably maintained at 2-8° C. during storage.

Alternatively, the BTX may be formulated as a nanoemulsion, see, e.g., U.S. Publication Nos. 2014/0099342; and 2012/0064136.

BOTOX® is a preferred BTX of the present disclosure. Unless the context should indicate otherwise, BOTOX® may be used herein to refer not only to BOTOX® itself but to any BTX as defined herein. Thus, BTX generally, and BOTOX® in particular, blocks neuromuscular transmission by binding to acceptor sites on motor or sympathetic nerve terminals, entering the nerve terminals, and inhibiting the release of acetylcholine. This inhibition occurs as the neurotoxin cleaves SNAP-25, a protein integral to the successful docking and release of acetylcholine from vesicles situated within nerve endings. When injected intramuscularly at therapeutic doses, BOTOX® produces partial chemical denervation of the muscle resulting in a localized reduction in muscle activity and spasticity. In addition, the muscle may atrophy, axonal sprouting may occur, and extrajunctional acetylcholine receptors may develop. There is evidence that reinnervation of the muscle may occur, thus slowly reversing muscle denervation produced by BOTOX®. When injected intradermally, BOTOX® produces temporary chemical denervation of the sweat gland resulting in local reduction in sweating. Following intradetrusor injection, BOTOX® affects the efferent pathways of detrusor activity via inhibition of acetylcholine release.

BTX/Ag Compositions

In one embodiment, the present disclosure provides a composition comprising water, BTX and colloidal silver particles. In another embodiment, the present disclosure provides a method of making a composition comprising water, BTX and colloidal silver. These compositions may be prepared by combining reconstituted BTX with colloidal silver particles and thoroughly mixing the combination to provide a homogeneous composition. The amount or concentration of BTX in the composition should be suitable for the intended medical or cosmetic use of the composition. In order to provide the desired concentration of BTX, the lyophilized BTX may be reconstituted with less than the total amount of desired aqueous phase, and then a volume of aqueous colloidal silver particles is added to the reconstituted BTX to provide the desired concentration of BTX.

The BTX/Ag compositions, which are also referred to herein as BB, may have from 10 to 600, or from 50 to 600, or from 100 to 600, or from 10 to 400, or from 50 to 400, or from 100 to 400, or from 10 to 200, or from 50 to 200, or from 100 to 200, or about 100 units of BTX. The concentration of the silver particles based on the weight of water in which the silver particles are suspended, may range from 1 to 100 ppm, or from 1 to 50 ppm, or from 1 to 30 ppm, or from 5 to 50 ppm, or from 5 to 40 ppm, or from 5 to 30 ppm, or from 10 to 100 ppm, or from 10 to 50 ppm, or from 10 to 30 ppm. As mentioned previously, the concentration of silver in the final composition may range, for example, from 1 to 100 ppm.

In one embodiment, increments of 100 Units of BTX, such as Ona Botulinum toxin A or any of the other Botulinum toxins commercially available, are reconstituted with aqueous silver particles, e.g., NMSH, having Ag in a range from 5 ppm-100 ppm per ml. Note that the current defacto standard for reconstitution of 100 Units of BTX is 0.9% Neutral Buffered Saline (NaCl). Thus, the Ag may be dissolved or suspended in neutral buffered saline (NaCl) prior to being combined with the BTX. For example, aqueous silver particles may be combined with the BTX in a range from 1 ml-2.5 ml silver having from 5-100 ppm silver per milliliter, such that one obtains the following exemplary dilutions and dosages, including ranges formed from these exemplary dilutions and dosages:

Dilution: 100 units BTX (e.g., Botox) with 1 ml 5 ppm aqueous silver solution;

Dilution: 100 units BTX with 1 ml of 10 ppm aqueous silver solution;

Dilution: 100 units BTX with 1 ml of 25 ppm aqueous silver solution;

Dilution: 100 units BTX with 1 mL of 50 ppm aqueous silver solution;

Dilution: 100 units BTX with 1 ml of 75 ppm aqueous silver solution;

Dilution: 100 units BTX with 1 ml of 100 ppm aqueous silver solution;

Dilution: 100 units BTX (e.g., Botox) with 2.5 ml 5 ppm aqueous silver solution;

Dilution: 100 units BTX with 2.5 ml of 10 ppm aqueous silver solution;

Dilution: 100 units BTX with 2.5 ml of 25 ppm aqueous silver solution;

Dilution: 100 units BTX with 2.5 mL of 50 ppm aqueous silver solution;

Dilution: 100 units BTX with 2.5 ml of 75 ppm aqueous silver solution;

Dilution: 100 units BTX with 2.5 ml of 100 ppm aqueous silver solution.

A preferred dosage is: 100 units BTX (e.g., Botox) diluted in 1 ml aqueous silver solution yields 10 units of Botox in 0.1 ml aqueous silver solution which does not change irrespective of the PPM aqueous silver solution.

Another preferred dosage: 100 units BTX (e.g., Botox) diluted in 2.5 ml aqueous silver solution yields 2.5 units of Botox in 0.1 ml aqueous silver solution which does not change irrespective of the PPM NMSTTO.

Addition dilutions includes from 1.0-5.0 ml of aqueous silver solution, including 0.1 increments therein, e.g., 1.1 ml, 1.2 ml., 1.3 ml, 1.4 ml, 1.5 ml, 2.0 ml, 2.5 ml, 3 ml, 3.5 ml, 4.0 ml, 4.5 ml, 4.6 ml, 4.7 ml, 4.8 ml, 4.9 ml of aqueous silver solution with increments of 100 Units Botox, where the aqueous silver solution has between 10 and 100 ppm of silver. For example, 50 units BTX (e.g., Botox) and 0.5 ml aqueous silver solution dilution yields a dosage of 10 U Botox per 0.1 ml aqueous silver solution. As another example, 200 Units BTX (e.g., Botox) and 2 ml aqueous silver solution dilution yields a dosage of 10 units Botox per 0.1 ml aqueous silver solution.

The dilution/dosage is dependent on the amount of diluent in mls that one adds to the container of BTX (e.g., Botox bottle) which has a fixed number of units so the dosage can vary. The more diluent one adds the more diluted the Botox becomes but this means that one has to inject a larger bolus of fluid trans-dermally depending on the desired number of units per injection site.

The present disclosure also provides BTX and solid silver particles, e.g., solid particles comprising Ag4O4, which may be reconstituted with water, such as buffered saline. The Ag4O4 particles can serve to encapsulate and/or stabilize the BTX during shipment, thus protecting it against bacterial and viral degradation and temperature denaturization. This combination of dry BTX and dry silver (e.g., Ag4O4) particles can be reconstituted in a doctor's office by the addition of buffer, saline, or just plain water. For example, 1 ml of pH adjusted sterile water can be added in a doctor's office to dilute the BTX to 100U in 1 ml or up to 2.5 ml of sterile water yielding the above noted dosages. As an alternative, some amount of water may be combined with the dry BTX and dry Ag4O4 particles, and the aqueous combination may be shipped to the doctor's office, whereupon the doctor adds additional water or buffer, etc. to provide the desired dosage of BTX and silver particles.

The addition of silver particles to BTX provides for advantageous compositions including increased efficacy (prolonged muscle relaxation upwards of 30% or greater (typically double the normal length of the so-called Botox effect which is normally 10-12 weeks) and increased shelf life of the reconstituted Botox—increase stability of the refrigerated product for several (3-4) months or more as compared to traditional Botox reconstituted with 0.9% NB saline which is 1-2 weeks. This is because the silver-containing diluent has inherent preservative capabilities because it is capable of both antibacterial and antiviral action so it can prevent contamination of the saline and the BTX once the BTX's bottle vacuum seal is broken. This prolongs storage because not only can it prevent CFUs from forming it can actually eliminate bacteria and virus contaminants if a sterile technique is not used.

The fact that the silver diluent of the present disclosure can provide increased efficacy time and longer stability for reconstituted BTX addresses two of the biggest drawback with the current state of the art. The BTX normally lasts 10-14 days after being reconstituted. The present diluent increases that shelf life by at least 1 day, or 2 days, or 3 days, or 4, days, or 5 days, or 6, days, or 7 days, or 8 days, or 9 days, or 10, days, or 11 days, or 12 days, or 13 days, or 14 days, or 15 days or more. Efficacy time and stability for reconstituted BTX may be evaluated with animal studies, e.g., with rats or mice. With rats or mice one could readily run stability tests and count the CFUS in the reconstituted Botox. One could also hook a patient up to EMGs with reconstituted diluent that has been stored for different periods of time with both saline versus aqueous silver solution and evaluate the efficacy of the muscle relaxation potential.

The BTX/Ag compositions of the present disclosure may be administered to a subject in need thereof, e.g., a human. However, care should be taken to ensure that no undesirable interactions occur between either of BTX or Ag, and other compounds or medicines that are being taken by the subject.

For example, undesirable interactions may occur between BTX and various agents, and likewise undesirable interactions may occur between colloidal silver and various agents. BTX may interact with aminoglycosides and other agents interfering with neuromuscular transmission so that co-administration of BOTOX® and aminoglycosides or other agents interfering with neuromuscular transmission (e.g., curare-like compounds) should only be performed with caution as the effect of the toxin may be potentiated. BTX may interact with anticholinergic drugs so that use of anticholinergic drugs after administration of BOTOX® may potentiate systemic anticholinergic effects. BTX may interact with other botulinum neurotoxin products. The effect of administering different botulinum neurotoxin products at the same time or within several months of each other is unknown. Excessive neuromuscular weakness may be exacerbated by administration of another botulinum toxin prior to the resolution of the effects of a previously administered botulinum toxin. BTX may react with muscle relaxants. Excessive weakness may also be exaggerated by administration of a muscle relaxant before or after administration of BOTOX®.

Regarding interactions with silver, it is noteworthy that preferred silver compositions of the present disclosure, such as AGRX®, do not contain cationic silver. The silver particles in AGRX® do not have a positive charge and will not interact with sodium chloride in normal saline to precipitate silver as insoluble silver chloride. Wounds may be cleansed with normal saline and then rinsed with a neutral solution. However, papain containing wound washes may be inactivated by silver-containing wound wash and should not be used concomitantly.

There are additional precautions and warnings that are associated with the administration of the BTX/Ag compositions of the present disclosure, which should be considered by the health care provider. There are no adequate and well-controlled studies in which BTX was administered to pregnant women. BOTOX® should be used during pregnancy only if the potential benefit justifies the potential risk to the fetus. When BOTOX® (4, 8, or 16 Units/kg) was administered intramuscularly to pregnant mice or rats two times during the period of organogenesis (on gestation days 5 and 13), reductions in fetal body weight and decreased fetal skeletal ossification were observed at the two highest doses. The no-effect dose for developmental toxicity in these studies (4 Units/kg) is approximately equal to the maximum recommended human dose of 400 Units on a body weight basis (Units/kg). When BOTOX® was administered intramuscularly to pregnant rats (0.125, 0.25, 0.5, 1, 4, or 8 Units/kg) or rabbits (0.063, 0.125, 0.25, or 0.5 Units/kg) daily during the period of organogenesis (total of 12 doses in rats, 13 doses in rabbits), reduced fetal body weights and decreased fetal skeletal ossification were observed at the two highest doses in rats and at the highest dose in rabbits. These doses were also associated with significant maternal toxicity, including abortions, early deliveries, and maternal death. The developmental no-effect doses in these studies of 1 Unit/kg in rats and 0.25 Units/kg in rabbits are less than the maximum recommended human dose of 400 Units based on Units/kg. When pregnant rats received single intramuscular injections (1, 4, or 16 Units/kg) at three different periods of development (prior to implantation, implantation, or organogenesis), no adverse effects on fetal development were observed. The developmental no-effect level for a single maternal dose in rats (16 Units/kg) is approximately 2 times the maximum recommended human dose based on Units/kg. It is not known whether BOTOX® is excreted in human milk. Because many drugs are excreted in human milk, caution should be exercised when BOTOX® is administered to a nursing woman.

As mentioned above, there are additional precautions and warnings that are associated with the administration of the BTX/Ag compositions of the present disclosure, which should be considered by the health care provider. Regarding administration of colloidal silver, e.g., AGRX®, there are no adequate and well-controlled studies in pregnant women. AGRX® is intended for external use only. If condition persists or worsens, medical attention may be required. AGRX® contains 10 PPM silver as nanocrystalline metallic particles and does not pose a risk for argyria.

Kits

In another aspect, the present disclosure provides a kit that comprises both botulinum toxin and colloidal silver particles in separate containers. For instance, the present disclosure a kit that comprises a container that holds botulinum toxin (BTX) and a container that holds colloidal silver particles and optionally also water. The kit may optionally contain further components that assist in the administration of the BTX and colloidal particles. For example, the kit may contain a syringe and needle that may be used to transfer the colloidal silver particles to the container of BTX. In addition, the kit may contain saline or aqueous buffer that may be used to reconstitute the BTX, if that BTX is in a powdered form. The kit may also include instructions for the use of the components in the kit and the administration of the BTX and colloidal silver particles to a patient.

Optionally, the kit comprises a container that comprises from 1 to 500, or 10 to 250, or about 100 units of BTX and a separate container that comprises colloidal silver at a concentration of from about 1 to 50 ppm, or about 5 to 40 ppm, or about 10 to 30 ppm. When the container that hold BTX has about 100 units of BTX then optionally the container that holds the colloidal silver has about 1 mL of water with about 1 to 50 ppm colloidal silver. The kit may optionally comprise yet another container that comprises water without colloidal silver, e.g., a buffer solution.

Methods of Use

The compositions of the present disclosure may be used for medical or cosmetic purposes. For example, they may be used for the treatment of strabismus, hemifacial spasms, cervical dystonia and blepharospasm. The compositions of the present disclosure may be used for the treatment of rhinitis, see, e.g., PCT Publication Nos. WO 2014/066916 and 2014/037531. The compositions of the present disclosure may be used for the treatment of premature ejaculation, see, e.g., WO 2014/031809. The compositions of the present invention may be used for the treatment of cerebrovascular disease, see, e.g., U.S. Publication No. 2014/0105883. The compositions of the present disclosure may be used for the treatment of migraine headache, see, e.g., PCT Publication No. WO 2013/137969. The compositions of the present disclosure may be used for the treatment of autonomic nervous system disorders, see, e.g., PCT Publication No. WO 2013/009625. The compositions of the present disclosure may be used for the treatment of esophageal spasms, see, e.g., PCT Publication No. WO 2013/009584. The compositions of the present disclosure may be used for the treatment of persistent genital arousal disorder, see, e.g., U.S. Publication No. 2012/0282241. The compositions of the present disclosure may be used for the treatment of sensory disturbance disorder, see, e.g., PCT Publication No. WO 2012/134897. The compositions of the present disclosure may be used for the treatment of a disease or condition caused by or associated with hyperactivity of muscles or exocrine glands, see, e.g., PCT Publication No. WO 2011/160826.

Accordingly, the present disclosure provides compositions that are pharmaceutical compositions comprising BTX and colloidal silver particles, where the pharmaceutical composition is sterile.

The changes in dosage are dependent on the dilution amount so when one knows how much is typically recommended to inject into a specific muscle then one adjusts the volume of the injection to deliver a specific number of Botox units. Each muscle is different but there are recommended guidelines which may be taken from the use of Botox in cosmetic applications. The maximum amount of Botox per injection site is usually no more than 50 units of Botox. In most muscles the reduction of muscle spasticity usually lasts no more than 10-12 weeks but the size of the muscle plays a role, and so that is why one will typically inject 5-8 units bilaterally into each the lateral orbicularis oris muscles around the eyes (squint lines on the side of the eyes) or 15-20 units into the Procerus muscles between the eyebrows or 30 units Botox into each of the two Masseter muscles, although the effect typically only lasts 10-12 weeks, unless silver particles are included in the administered formulation according to the present invention. These same approximate amounts may be used for the therapeutic methods according to the present disclosure.

The present disclosure, which provides composition and uses of BTX in combination with silver particles, may increase the desired effect achieved from BTX alone by a factor of 25%, or 50%, or 75%, or 100%, or 150%, or 200%, or 250%, or 300% based on traditionally recommended injection volumes of Botox units.

The ability of the silver particles to preserve reconstituted Botox for therapeutic and cosmetic applications is very important because one can improve sterility issues associated with withdrawals for multiple patients from the same bottle and the solution lasts longer and is therefore more cost effective.

The ability of the silver particles to extend the efficacy of a BTX injection for therapeutic or cosmetic applications is advantageous because fewer injections are required over time.

Someone who is injected with Botox that is reconstituted with 0.9% NB saline has an onset time for muscle relaxation of usually about 7-10 days, at which time one observes either a reduction in wrinkles or less muscle contraction i.e., less muscle spasm and less clenching or headache. The compositions and methods of the present disclosure may reduce that onset time down to as little as 3-5 days before these same signs manifest themselves.

The compositions of the present disclosure may be used for cosmetic purposes, e.g., to reduce the appearance changes associated with aging, i.e., for anti-aging effect, see, e.g., PCT Publication No. WO 2011/154126. Aging is associated with the development of lines and wrinkles caused by actinic damage, gravitational effect, sleep lines, and muscular action. Mimetic facial musculature may undergo hypertrophy secondary to hyperfunctional pull. BTX injections reduce facial lines caused by hyperfunctional muscles. They also are used to contour aspects of the face such as the brows. The compositions of the present disclosure may be used for the cosmetic purposes for which BTX is used. For example, a composition of the present disclosure may be used to treat infraorbital dark circles, see, e.g., US Publication No. 2012/0115792.

In one embodiment, the present disclosure provides for enhanced reduction of wrinkles compared to using BTX alone for this condition. Reduction of wrinkles may be objectively measured by the use of EMGs, comparing baseline readings before injection of the reconstituted botox then an objective biometric measurement of the reduction in muscle contraction over time then noting how long it takes for that muscle contraction to return to baseline levels. The muscle relaxation is the key. The result of this is a subjective visual assessment in the reduction of wrinkles in the epidermal and dermal tissues the lay over that particular muscle.

In one embodiment, the present disclosure provides for reduction in TMJD compared to using BTX alone for this condition. Reduction in TMJD may be objectively measured by the use of EMGs, comparing baseline readings in the masseter and anterior temporalis muscles before injection of the reconstituted botox then an objective biometric measurement of the reduction in muscle contraction in the masseter and temporalis anterior muscles over time then noting how long it takes for that muscle contraction to return to baseline levels. Elevated muscle contraction in both the temporalis and the masseter muscles results in clenching and grinding of the teeth and jaws which leads to the torqueing and twisting and retrusion of the mandible which results in excessive compression of the disco-condylar complex (known as the TM Joints). There is a high degree of causality between clenching and grinding and degeneration of the disk, displacement of the TMJ disk, and related osteoarthritic changes in the boney architecture of the joint complex.

In one embodiment, the present disclosure provides for reduction in clenching compared to using BTX alone for this condition. Reduction in clenching may be objectively measured by the use of EMGs, comparing baseline readings in the masseter and anterior temporalis muscles before injection of the reconstituted botox then an objective biometric measurement of the reduction in muscle contraction in the masseter and temporalis anterior muscles over time then noting how long it takes for that muscle contraction to return to baseline levels. This same approach may be used to objectively measure a reduction in nocturnal bruxism which is achieved with the compositions and according to the methods of the present disclosure.

In the forgoing, a reduction of about 15-20% in the average muscle contraction values expressed in microvolts per second for that particular patient over the length of the scan which typically 15 seconds is considered a reduction in wrinkles, TMJD, etc.

In one embodiment, the present disclosure provides for reduction in viral herpetic lesions such as Herpes Simplex One and Varicella Zoster compared to using BTX alone for this goal. Reduction in viral infection may be subjectively measured by over time or by reduction in time as to the presence of the lesion and how much less time it takes to resolve. Anti-viral tests can be run in vitro.

BOTOX® in combination with colloidal silver as disclosed herein, e.g., AGRX®, is an acetylcholine release inhibitor and a neuromuscular blocking agent. BOTOX® combined colloidal silver, e.g., with Ag4O4 Silversol (10 PPM) may, according to the present invention, be used for long term efficacy treatment of: Treatment of overactive bladder (OAB) with symptoms of urge; urinary incontinence, urgency, and frequency, in adults who have an inadequate response to or are intolerant of an anticholinergic medication; Treatment of urinary incontinence due to detrusor over-activity associated with a neurologic condition [e.g., spinal cord injury (SCI), multiple sclerosis (MS)] in adults who have an inadequate response to or are intolerant of an anticholinergic medication; Prophylaxis of headaches in adult patients with chronic migraine (≥15 days per month with headache lasting 4 hours a day or longer); Treatment of spasticity in adult patients; Treatment of TMJD (Temporomandibular joint dysfunction) by reduced clenching and grinding forces exerted on the TMJoints through relaxation of the masseter muscles; Treatment of cervical dystonia in adult patients, to reduce the severity of abnormal head position and neck pain caused by chronic repetitive muscle spasms; Treatment of severe axillary hyperhidrosis that is inadequately managed by topical agents in adult patients; Treatment of blepharospasm associated with dystonia in patients ≥12 years of age; Treatment of strabismus in patients ≥12 years of age. The present disclosure provides methods of treating these conditions in a patient in need thereof by administering an effective amount of a composition comprising BTX and colloidal silver as disclosed herein. However, safety and effectiveness of BOTOX have not been established for: Prophylaxis of episodic migraine (14 headache days or fewer per month); Treatment of upper or lower limb spasticity in pediatric patients; Treatment of hyperhidrosis in body areas other than axillary; Reduction of wrinkles in the dermal tissues which lay over the muscles of facial expression including orbicularis oculi, procerus, Occipitofrontalis, nasalis, and orbicularis oris, Thus, for example, in one aspect, BOTOX® (OnabotulinumtoxinA) is used in combination with a silver-containing buffer, e.g., a buffer of 10 ppm AGRX Wound Wash (K151185), for the indication of pain relief of Temporomandibular Joint Dysfunction (TMJD), e.g., for relief of pain associated with the masseter muscle. The detrimental clinical effects of nocturnal bruxism (which includes clenching and grinding) on the health and integrity of the temporomandibular joints has been well-established in the literature. Excessive contraction by the major elevator muscles—namely the bilateral masseter muscles—not only results in attrition and wear to the patients dentition but, can also lead to damaging compressive forces within the disco condylar complexes off the temporomandibular joints. Such excessive forces can over time lead to irreversible damage of those muscles, ligaments, tendons and articular joint surfaces involved in mandibular movement. Signs and symptoms of early onset TMJD (which are often reversible) include headaches, neck and shoulder pain, limited opening, jaw pain, clicking and popping sounds within the joint itself and anterior disk displacement with reduction. As the signs and symptoms of TMJ D progress, the Temporo Mandibular joint complexes begin to undergo non-reversible, osteoarthritic, degenerative changes which include anterior disc displacement without reduction, disk perforations and adhesions, closed locks, further reduction in mandibular movement, deviations and deflections on opening and closing, muscle pain and permanent changes to the bony architecture of the condyle and articular eminence of the TM Joints. The long-term effects of uncontrolled clenching and grinding due to nocturnal bruxism can not only impact the patient's ability to open and close their mandible normally but, also their ability to breathe, eat, chew and swallow in a normal pain free manner. Since the masseter muscles are the major elevator muscles responsible for joint compression due to clenching grinding and since the effect of Botox injections into these same masseter muscles has been clinically demonstrated to partially reduce masseter muscle contraction for only a limited period of time (on average 3-4 months).

In one embodiment, BTX/Ag may be used in the treatment of neuralgias. Due to powerful anti-inflammatory effect of nano-metallic silver hydrosol (NMSH), subcutaneous and intramuscular injection of BTX/Ag 10 ppm into affected dermatome can be utilized for pain relief.

In one embodiment, BTX/Ag may be used in combination with an injectable NSAID. Due to powerful anti-inflammatory effect of NMSH the combination of BTX/Ag 10 ppm can significantly decrease inflammation due to post-surgical swelling. Due to powerful anti-inflammatory and anti-infective benefit of NMSH, the combination of BTX and 10 ppm Ag can significantly decrease inflammation due to either chronic or acute infection. Traditional steroids are no clinical benefit in combination with antibiotics for this purpose as they suppress the immune system and counteract the effect of the antibiotic—whereas NMSH has been shown in the literature to be synergistic and potentiating with 18 different classes of antibiotics making it wholly complimentary with antibiotics in the treatment of infection. The added benefit of the BTX/Ag is muscle relaxation and reduced muscle movement while the tissues are healing.

The administration of a composition of the present disclosure to a subject in need of a medical or cosmetic treatment may follow standard methods for BTX administration. See, e.g., the protocols disclosed in PCT Publication No. WO 2012/103415. The subject may be a human, or the subject may be a non-human mammal or bird.

The use of aqueous silver solutions as disclosed herein, as a diluent for reconstituting BTX, is advantageous because the presence of the silver provides for a reduction of inflammation and irritation at the injection site; less redness and swelling due to decreased dilution and increased dosage (less of a fluid bolus) therefore less risk of wheel and flare reaction at the injection site. There is also less risk of infection post injection due to the inherent antibacterial nature of the aqueous silver solution. There is, for example, no need to pre wipe and disinfect the injection site with 70% isopropyl alcohol prior to injection of the reconstituted Botox because the aqueous silver particles achieve that antibacterial effect.

Analytical Methods

The analysis of the silver content in the compositions of this invention may be done by atomic absorption (AA), inductively coupled plasma/atomic emission (ICP/AES), or other techniques known to one of ordinary skill in the art to be sensitive to silver in the appropriate concentration range. If the particles of the silver composition are small and uniformly sized (for example, 0.01 micrometers or less), a reasonably accurate assay may be obtained by running the colloid directly by AA or ICP/AES. This is because the sample preparation for AA ionizes essentially all of the silver allowing its ready detection. If the compositions comprise particles as large as 0.2 micrometers, it is preferred to use a digestion procedure. The digestion procedure is not necessarily ideal for silver compositions that may have been manufactured or stored in contact with halides or other anionic species that may react with finely divided silver, or combined with protein or other gelatinous material.

An embodiment of the digestion procedure is as follows: (a) take a 10 ml aliquot of a thoroughly mixed or shaken silver composition to be analyzed, and place it in a clean polycarbonate bottle or other container of suitable material (generally, the bottle) with a tight fitting lid. A size of 30-100 ml is preferred; (b) with a micropipette or dropper, add 0.1 ml of nitric acid, reagent grade to the silver composition in the bottle; (c) with the lid of the bottle tightly in place, heat the composition to 80° C. with mild agitation for a time sufficient to dissolve the silver—dissolution is essentially instantaneous; (d) allow the resulting mixture to cool to room temperature with the lid in place. Shake the bottle thoroughly; (e) utilize AA, ICP/AES, or equivalent means to analyze the silver content of the composition. Preferably, one will utilize a freshly prepared standard or standards, preferably prepared according the equipment manufacturer's instructions, with appropriate dilution as needed. When reporting results, one must take into account all dilutions during preparation, including the 1% dilution caused by addition of the nitric acid.

The analysis of the physical and chemical form of the silver in the compositions may be done by time-of-flight secondary ion mass spectrometry (TOF-SIMS). The TOF-SIMS technique is suitably used as a survey tool to identify the composition of unknown samples. It is capable of quantification if the appropriate microanalytical standards are available for calibration. To perform TOF-SIMS analysis, a few drops of a silver-containing composition are evaporated to dryness on a silicon substrate at ambient temperature. The residue is analyzed by TOF-SIMS. A reference silver (II) oxide (AgO) material is analyzed by placing a few particles of the reference powder as received from the vendor on a silicon substrate, and is denoted as the reference. The time-of-flight secondary ion mass spectrometry technique (TOF-SIMS) is based on the principle of bombarding a solid sample with a pulsed, finely focused beam of primary ions, and then analyzing the secondary ions produced from the surface of the sample via a time-of-flight mass spectrograph. This analytical technique is surface sensitive, deriving its information from a layer that extends to approximately 20 to 40 Å below the surface.

Size/Morphology/Composition Analysis may be performed by any of SEM, EDS (EDAX) and TEM. In particular, the silver/water compositions may be dried and placed on an EM grid and examined in an SEM (i.e., Scanning Electron Microscope) and two different TEMs (i.e., Transmission Electron Microscopes). For example, a silver/water composition may be placed onto C-film and examined by a cryo-TEM at a temperature of about −100° C. using a power level of approximately 100 kV. The silver/water composition of the present invention was therefore substantially instantly frozen. As another example, TEM analysis may be performed in the "SAD" mode. As yet another example, an EDAX spectrum (i.e., an Energy Dispersion Spectrum or "EDS") of silver particles taken from silver/water compositions of the present invention may be used to check for metallic contaminants. In one aspect, the colloidal silver particles do not contain gold or platinum.

EXAMPLES

Background:

Botox cosmetic (Botulinum Toxin A) is commercially available in 100 unit doses. Traditionally, a container of 100 units of attenuated botulinum toxin A cosmetic is diluted with about 1 mL of an inert aqueous carrier, typically saline, and then gently agitated. An intended injection site of a patient is cleaned with isopropanol. A desired amount of this diluted botox cosmetic is injected into a patient. In the following examples, the traditional saline carrier was replaced with an aqueous suspension of nanometallic silver particles as described herein, where this active aqueous carrier had a silver concentration of either 10 ppm or 30 ppm. This silver particle-containing diluted botulinum toxin A of the present disclosure will be referred to herein for convenience as BB. The aqueous nanometallic silver suspension is commercially available from American Biotech Labs as their HYDROSOL product. In addition, the intended injection site was wiped with a sterile solution of 10 ppm HYDROSOL rather than with isopropanol. Every patient in the following examples understood the experimental nature of the treatment and signed an Informed Consent For Treatment document and a non-disclosure agreement. Each injection contained 10 units of the diluted botulinum toxin A.

A total of 1469 units of Botox diluted with silver nanoparticles ("BB") were injected into the various facial muscles of 17 different patients over a 24 month period. Patients were evaluated at the day of injection, then at 7 and 21 days post injection, then at 45 day intervals thereafter. Assessment of Botox effect was determined subjectively by the injector as indicated by: the range of motion/ amount of muscle activity and presence or absence of either static or functional wrinkles.

Example 1

Patient No. 1 received 44 units of BB made from 30 ppm HYDROSOL suspension. These units were injected bilaterally around the eyes, mouth and forehead. The effect of the botox lasted for 8.5 months. The patient reported a slight stinging and discomfort at the injection sites. About 10 months after receiving the 44 units of BB, the patient received 40 units of BB made from 10 ppm HYDROSOL, where these units were injected bilaterally around the eyes and into the forehead/procerus muscles and philtum. The patient did not report any stinging or discomfort from the injections. The effect of the Botox lasted for more than 10+ months. No erythema was observed.

This patient had previously received several Botox treatments where the diluent was 0.9% Neutral Buffered Saline, in these same areas. The average length of the Botox effect from these injections was 4-5 months. Accordingly, the combination of Botox and silver nanoparticles according to the claimed invention results in a significantly longer-duration Botox effect compared to traditional Botox injections.

Example 2

Patient No. 2 received 45 units of BB made from 30 ppm HYDROSOL suspension. These units were injected bilaterally around the eyes, mouth and forehead. The effect of the botox lasted for 7.5 months. The patient reported a slight stinging and discomfort at the injection sites. About 10 months after receiving the 45 units of BB, the patient received 42 units of BB made from 10 ppm HYDROSOL, where these units were injected bilaterally around the eyes and into the forehead. The patient did not report any stinging or discomfort from the injections. The effect of the botox lasted for 9 months.

During the five years previous to receiving injections of BB as described above, this patient had previously received many Botox treatments where the diluent was 0.9% Neutral Buffered Saline, in these same areas. The average length of the Botox effect from these injections was 4-5 months. Accordingly, the combination of botox and silver nanoparticles according to the claimed invention results in a significantly longer-duration botox effect compared to traditional botox injections.

Example 3

Patient No. 3 received 34 units of BB made from 30 ppm HYDROSOL suspension. These units were injected bilaterally around the eyes and forehead. The effect of the botox lasted for 8.5 months. The patient reported a slight stinging and discomfort at the injection sites. About 50 weeks after receiving the 34 units of BB, the patient received 50 units of BB made from 10 ppm HYDROSOL, where these units were injected bilaterally around the eyes and into the forehead. The patient reported a slight discomfort at the injection sites. The effect of the botox lasted for at least 11 months. No erythema was reported.

This patient had previously received two Botox treatments where the diluent was 0.9% Neutral Buffered Saline, in these same areas. The average length of the Botox effect from these injections was 5-6 months. Accordingly, the combination of botox and silver nanoparticles according to the claimed invention results in a significantly longer-duration botox effect compared to traditional botox injections.

Example 4

Patient No. 4 received 34 units of BB made from 10 ppm HYDROSOL suspension. These units were injected bilaterally around the eyes, forehead and the left side of the upper lip. The effect of the botox lasted for 8.5 months. The patient reported a slight stinging and discomfort at the injection sites. About 11 months after receiving the 34 units of BB, the patient received 50 units of BB made from 10 ppm HYDROSOL, where these units were injected bilaterally around the eyes and into the forehead. The patient reported a slight discomfort at the site of the injections. The effect of the botox lasted for at least 10 months.

Previous to receiving injections of BB as described above, this patient had received numerous Botox treatments where the diluent was 0.9% Neutral Buffered Saline, in these same areas. No stinging or discomfort was noted at the injection sites. The average length of the Botox effect from these injections was 5-6 months. Accordingly, the combination of botox and silver nanoparticles according to the claimed invention results in a significantly longer-duration botox effect compared to traditional botox injections.

The preceding examples demonstrate that colloidal silver may be used in conjunction with botulinum toxin A to extend the muscle relaxant efficacy of BOTOX, an exemplary botulinum toxin. In addition, these studies demonstrate that colloidal silver may be used in lieu of isopropanol to provide a sterile skin surface for injections.

Example 5

A clinical trial is described which evaluates the safety and efficacy of BOTOX® (onabotulinumtoxinA) and the buffer of AGRX® 10 PPM Ag4O4 Silversol™ in human participants. The goal of this trial is to illustrate the dosage and efficacy between the BOTOX® (onabotulinumtoxinA) and the buffer of AGRX® 10 PPM Ag4O4 Silversol™ solution and the indication of reduced clenching due to nocturnal bruxism over a 12 month period. Safety of the participants is a primary goal of this trial; along with dosage amounts and average efficacy. In addition, this trial will test the hypothesis that the wound healing and anti-inflammatory capabilities of a colloidal silver composition as disclosed herein, e.g., the AGRX® Ag4O4 Hydrosol, may affect certain connective tissue and enzyme cascades within the muscle spindles in such a way as to extend the useful life and effect of the Botox solution (muscle relaxation) by affecting the levels of ISL and LoX. This trial will also test the hypothesis that a colloidal silver composition as disclosed herein, e.g., the AGRX® Ag4O4 Hydrosol solution, has an anti-infective effect on the surrounding dermal tissues when injecting Botox Bacteriostatic and is capable of replacing the use of IPA. Thus, in one embodiment, the present disclosure provides a method for reducing clenching due to nocturnal bruxism, the method comprising administering to a patient in need thereof, a therapeutically effective amount of BOTOX and colloidal silver, e.g., AGRX® 10 PPM Ag4O4 Silversol™.

The compositions of the present disclosure may be used to extend the period of time of muscle relaxation that may be induced by Botox. The objective of this clinical trial is demonstrate that we can utilize a diluent solution of nanometallic silver hydrosol to help extend the useful time of useful Botox effect in the masseter muscles. The impact of that is that such a solution would make a meaningful clinical impact on limiting the effects that nocturnal bruxism could have in the progression of Temporo Mandibular Joint Dysfunction. This study sets forth a clinical protocol to objectively and analytically compare biometric data which can be collected demonstrating the length of Botox effect on the Masseter muscles when two distinctly different diluent solutions are utilized using an identical protocol.

The medicinal agents used in this study include BOTOX® (OnabotulinumtoxinA)—100-unit vial and 10 PPM AGRX® Solution Antibacterial Silver Skin and Wound Cleanser (AGRX®—ABL Medical) reconstituted with buffer—2.50 ml. Other sources of Botox and aqueous colloidal silver particles may be used in the practice of the present invention, however AGRX® is a preferred aqueous colloidal silver gel composition for reasons including those provided below. The Botox used in the study is a *Clostridium botulinum* type A neurotoxin complex, with 0.5 mg of Albumin Human Active (vacuum-dried form without a preservative) and is used in combination with AGRX® 10 ppm Ag4O4 (10 ppm suspended in solution) diluted with purified H2O.

AGRX® Ag4O4 Hydrosol is a colloid of nano-metallic silver particles (Ag4O4 coating a Ag core approximately 30 nm in diameter) blended with ultra-pure water with a neutral pH. The AGRX® Ag4O4 Hydrosol has some very unique wound healing, anti-infective and anti-inflammatory properties which make it ideally suited for use in compositions and methods of the present disclosure. The inventor has successfully performed over 15,000 peri-osseous surgeries and has recorded notable improvements in the rate of wound repair and resolution of infection the AGRX® Ag4O4 Hydrosol its efficacy and performance is undeniable. The fact that an increased rate of epthelialization and wound closure is often noted immediately after surgery appears to indicate that the AGRX® Ag4O4 Hydrosol is somehow stimulating or activating stem cell activity. In much the same manner, the AGRX® Ag4O4 Hydrosol appears to be having an effect on fibroblast formation and connective tissue metabolism and the essential role that fibrogenesis plays in normal muscle metabolism.

Without intending to be bound, the inventor provides the following hypothesis. There are numerous inhibitors of LoX and c.t. metabolism and one of them is an enzyme by product of the Glucaronic Acid cycle (Anaerobic metabolism) called Iso Citrate Lyase ("ISL"). ISL is a negative inhibitor of LoX and is capable of preventing the cross-linking and maturation of normally dense cross linked collagen. AGRX® Ag4O4 Hydrosol appears to negatively inhibit the formation of ISL and contemporaneously promote the formation of Lysol oxidase ("LoX") which is a key driver in the formation of normal mature cross linked collagen. When ISL is turned off or inhibited and the concentration of lysol oxidase in the tissue is adequate, the c.t. is able to adequately support the surrounding muscle tissue and prevent it from having to work as hard—this helps prevent muscle fatigue and muscle spasm both of which negatively impact and shorten the length of time of the Botox effect. The corollary of this, is that the use of AGRX® Ag4O4 Hydrosol can be used to stimulate ISL levels, thereby positively impacting connective tissue metabolism and thereby helping to lengthen the useful the period of time of the Botox effect by providing better connective tissue support for the muscle spindle. There is also noticeably less erythema and localized swelling as well as less skin irritation when the AGRX diluent is utilized. It is believed that this is due to the anti-inflammatory, and disinfectant properties of the AGRX molecule suspended in purified water.

For this trial, AGRX® 10 ppm Ag4O4 (10 ppm suspended in solution) solutions shall be gamma sterilized. Documentation and all regulatory compliance for sterilization process shall be supplied with delivery of the product. BOTOX® has a two (2) year shelf life in sterile, vacuum-dried state. After combining AGRX® 10 ppm Ag4O4 (10 ppm suspended in solution) diluent of purified H2O, the shelf life is about 4 hours.

Regarding BOTOX®, dosing in initial and sequential treatment sessions should be tailored to the individual based on the size, number and location of muscles involved, severity of spasticity, the presence of local muscle weakness, the patient's response to previous treatment, or adverse event history with BOTOX®. The recommended dilution is about 200 Units/4 mL or 100 Units/2 mL with preservative-free 0.9% Sodium Chloride Injection, USP. The lowest recommended starting dose should be used, and no more than 50 Units per site should generally be administered. An appropriately sized needle (e.g., 25-30 gauge) may be used for superficial muscles, and a longer 22 gauge needle may be used for deeper musculature. Localization of the involved muscles with techniques such as needle electromyographic guidance or nerve stimulation is recommended.

Repeat BOTOX® treatment may be administered when the effect of a previous injection has diminished, but generally no sooner than 12 weeks after the previous injection. The degree and pattern of muscle spasticity at the time of re-injection may necessitate alterations in the dose of BOTOX® and muscles to be injected.

For Upper Limb Spasticity, doses ranging from 75 Units to 400 Units are divided among selected muscles at a given treatment session. The following are recommended dose, total dosage, and number of sites for various muscle areas: Biceps Brachii—100 Units-200 Units divided in 4 sites; Flexor Carpi Radialis—12.5 Units-50 Units in 1 site; Flexor Carpi Ulnaris—12.5 Units-50 Units in 1 site; Flexor Digitorum Profundus—30 Units-50 Units in 1 site; Flexor Digitorum Sublimis—30 Units-50 Units in 1 site; Adductor Pollicis—20 Units in 1 site; Flexor Pollicis Longus—20 Units in 1 site.

For Lower Limb Spasticity, doses ranging from 300 Units to 400 Units are divided among 5 muscles (gastrocnemius, soleus, tibialis posterior, flexor hallucis longus and flexor digitorum longus) at a given treatment session. The following are recommended dose, total dosage, and number of sites for various muscle areas: Gastrocnemius medial head—75 Units divided in 3 sites; Gastrocnemius lateral head—75 Units divided in 3 sites; Soleus—75 Units divided in 3 sites; Tibialis Posterior—75 Units divided in 3 sites; Flexor hallucis longus—50 Units divided in 2 sites; Flexor digitorum longus—50 Units divided in 2 sites.

Regarding AGRX®: AGRX® is a proprietary formulation of silver (nano-silver at 0.01 micron in purified water) admixed with purified H2O that contains 10 part per million (ppm) molecular silver (American Biotechnology Labs, LLC; Alpine, Utah). AGRX® is FDA cleared—K151185. AGRX Wound Wash Antibacterial Silver Skin and Wound Cleanser is Indicated for prescription use—to cleanse, moisten and irrigate skin and dermal lesions; Stage I-IV pressure ulcers, stasis ulcers, diabetic ulcers, foot ulcers, post-surgical wounds, medical device insertion sites, donor and recipient graft sites, first and second degree burns, cuts, abrasions and minor skin irritations. It also aids in removal of excessive skin oils, dirt and debris, and is an effective cleansing solution. Federal law restricts this device to sale by or on the order of a licensed healthcare practitioner.

Clinical Recommendations: AGRX® should be recommended for formulary inclusion because it offers numerous unique and distinct, patented characteristics when compared to currently available silver wound washes. Feature of AGRX® include: 1. Pure, crystalline, metallic silver approximately 10 to 15 nanometers in size; 2. Each nanoparticle of silver is covered by an Ag4O4—Ag• oxide positive charged coating; 3. The silver oxide coating separates the nanocrystalline silver particles by 2 to 3 nanometers and allows them to attract electrons individually; 4. The nanoparticles resonate a frequency that has been thought to kill microbes and possibly explains the catalytic action that sustains the biocidal action of AGRX® after the silver oxide coating strips away; 5. Produces rapid and continuous bactericidal activity; unlike conventional wound washes that become inactive once all silver cations are neutralized; 6. The only silver wound wash FDA-cleared to inhibit MRSA and VRE; 7. Low 10 PPM silver concentration and will not stain the skin or pose a risk for argyria; 8. No known or expected adverse events; 9. Aqueous solution formulation may facilitate autolytic debridement of necrotic tissue so may allow for injection into infected tissue; 10. Contains no sulfa or alcohol; 11. Non-flammable; and 12. May be used with hyperbaric oxygen therapy.

Participants: 17 Patients were treated with Botox Cosmetic (Botulinum Toxin A) in combination with AGRX® Ag4O4 Hydrosol diluted 1 ml to 100 u Botox. 5 Patients were treated and followed over a 24 month period with Botox Cosmetic (Botulinum Toxin A) in combination with 30 ppm AGRX® Ag4O4 Hydrosol diluted 1 ml to 100 u Botox. 12 Patients were treated over a 24 month period with Botox Cosmetic (Botulinum Toxin A) in combination with 10 ppm AGRX® Ag4O4 Hydrosol diluted 1 ml to 100 u Botox.

All 17 patients sign Informed consent for treatment documents and non-disclosure agreements. All 17 patients understood that the use of AGRX® Ag4O4 Hydrosol as a Botox diluent was not a listed indication of such a drug and that this trial was experimental in nature. All 17 patients were recruited, informed, consented and cared for as prescribed under the INTERNATIONAL CONFERENCE ON HARMONISATION OF TECHNICAL REQUIREMENTS FOR REGISTRATION OF PHARMACEUTICALS FOR HUMAN USE Guidelines. No adverse events or adverse drug reactions were observed and no patients reported such events during the period from treatment times to the 2 year follow up.

The protocol included testing two investigational products.

Investigational Product #1: One ml of the 30 ppm AGRX® Ag4O4 Hydrosol solution was injected into a sterile 100 u bottle of attenuated Botulinum Toxin A (Botox Cosmetic) and gently agitated. Injection sites were wiped with a sterile solution of 30 ppm AGRX® Ag4O4 Hydrosol. 10 units of prepared Botox Bacteriostatic were drawn up at a time in separate syringes and injected.

Investigational Product #2: One ml of the 10 ppm AGRX® Ag4O4 Hydrosol solution was injected into a sterile 100 u bottle of attenuated Botulinum Toxin A Botox Cosmetic) and gently agitated. Injection sites were wiped with a sterile solution of 10 ppm AGRX® Ag4O4 Hydrosol. 10 units of prepared Botox Bacteriostatic were drawn up at a time and injected.

A total of 1469 units of Botox were injected into the various facial muscles of 17 different patients over a 24 month period including procerus, lateral occipitofrontalis, orbicularis oculi and orbicularis oris. Patients were tracked day of injection then at 7 and 21 days post injection, then at 45 day intervals thereafter. Assessment of Botox effect was determined subjectively by the injector as indicated by; the range of motion/amount of muscle activity and presence or absence of either static or functional wrinkle lines.

There appeared to be a clinically significant (noticeably longer lasting) Botox effect when the nanometallic silver hydrosol (NMSH) was used as a diluent in both the 10 ppm and 30 ppm concentrations however, the 10 ppm appeared to produce longer lasting effects than the 30 ppm solution. The BTX/Ag 30 ppm solution appeared to produce more localized discomfort at the injection site than the corresponding 10 ppm solution. There was noticeably less erythema and wheel and flare present at the injection site after the BTX/Ag 10 ppm and 30 ppm was injected.

Post Injection, there was a clinically significant increase in the useful life of the BTX/Ag in all 17 patients. In some patients this effect was almost double that of Botox Cosmetic using a diluent of 0.9% Neutral Buffered Saline.

Safety: No adverse events or adverse drug reactions were observed at the time of treatment or in post procedure follow ups of 2 years. No other side effects were observed in all 17 patients.

The dosage range summary: OnabotulinumtoxinA (100 u) should remain as previously approved in historical drug research and drug indications. The simple replacement of colloidal silver solution, e.g., NMSH such as AGRX® Ag4O4 Hydrosol or Tetrahedral Tetroxide Silver Solution 1 ml for the 0.9% Neutral Buffered Saline has shown clinical significance in both efficacy and safety. The study did not illustrate a clear difference between the 10 PPM arm and the 30 PPM arm in regards to effective time periods. No other differences were noted between the arms in regards to safety, performance or comfort. The 1:1 replacement ratio from currently approved drug has been illustrated to provide both a safe bench mark and protocol standard. In addition, the studies protocol has shown a marked improvement in both performance and participant comfort and participant satisfaction.

Furthermore, in one embodiment, the present disclosure provides an injectable anti-viral solution comprising BOTOX and colloidal silver as disclosed herein, and a method of using the solution in the treatment of viral infection. With Botox solutions diluted with 0.9% Neutral buffered saline Allergan, Inc., warns against injecting Botox solutions into and around areas of infected tissue (due to a concern over spreading the infection). 2 of the 17 patients described above that were treated with Botox and NMSH had small Herpes type 2 cold sore outbreaks of their lips when we first injected the Botox+NMSH into the surrounding peri-oral musculature. Since this time neither patient has had any further cold sore outbreaks. It is believed that this clinically proven anti-viral capability of the NMSH according to the present disclosure may have helped to eradicate the virus. This anti-viral capability is an unexpected use of the BTX/Ag compositions of the present disclosure. Thus, in one embodiment the present disclosure provides a method of treating a viral infection in a patient, where the method comprises administering a combination comprising BTX, e.g., BOTOX® and colloidal silver particles in an effective amount to reduce viral infection.

A phase 2 clinical trial in the form of a parallel three (3) arm randomized, double blind factorial study with 40 participants per arm is performed. Arm 1: 40 participants receiving bilateral masseter muscle injections of BOTOX® and AGRX® combination treatment. Arm 2: 40 participants receiving unilateral masseter muscle injection of BOTOX® and receiving unilateral masseter muscle injection AGRX® combination treatment. Arm 3: 40 participants receiving bilateral masseter muscle injections of BOTOX® treatment. Myotronics dermal emgs may be used as baseline.

By using a 3 arm double blinded, factorial study there can be provided a direct comparison between the effects and clinical results of muscle relaxation with Botox diluted with saline and Botox diluted with colloidal silver as disclosed herein, e.g., NMSH, e.g., AGRX. The primary objective is to specifically measure the exact dynamics of the masseter muscle and at what rate and level of range of motion changes and exactly how this has been modified by the BOTOX® and AGRX® combination treatment. A secondary objective is to exactly measure the length of time to amount of efficacy of the BOTOX® and AGRX® combination treatment. A tertiary objective is to measure the levels of participant satisfaction with the overall treatment results and the participants' overall satisfaction with the treatment experience.

The estimated study duration that served as the assumption for sample size calculations is twelve (12) months. All randomized participants will be followed to a common study end date, which is estimated to occur when the last randomized patient has been followed for eighteen (18) months, based on a one (1) month recruitment period. Interim analysis during this study shall be conducted for each participant on the following schedule: once prior to Botox injections to establish baseline biometrics then at 10 days after Botox injection followed by every 28 days until noticeable muscle spasticity starts returning to one or more of the patients masseter muscles or as requested by the Medical Officer. This analysis schedule will ensure participant safety before the other participants enter into the trial as well as fulfill the trial objectives.

Based upon the anticipated event rates, premature treatment discontinuation and expected relative efficacy, approximately 120 participants will be enrolled in the study, with approximately 40 participants in each arm. Inclusion criteria include the following: 1. Written informed consent obtained; 2. Men and women aged 18 or older; 3. Patient ASA Physical Status Classification of 2 or less with any itemized co-morbidity factors and or prescription drugs; and 4. Clinical diagnosis of either Clenching, Grinding, Nocturnal Bruxism and or Temporomandibular Joint Dysfunction—chronic or acute. Exclusion criteria include the following: any patient that has a clinical diagnosis of Ankylosing Spondylitits, Cervical Dystonia, Multiple Shclerosis, ALS, Parkinsons Disease, or any neuro-endocrine disorder such as Ricketts or Pagets Disease; any patient with a neuromuscular disorder such as myasthenia gravis or Lambert-Eaton syndrome; Any patient with Cardio Vascular Disease requiring use of a pacemaker; any patient that has a clinical diagnosis of Osteoarthritis of the TMJD or Rheumatoid arthritis; any patient that has undergone surgery to either of the TM Joints; any patient with serious head or neck trauma; any patient who has been involved in an MVA within the past 24 months or whom is still seeking active treatment for this accident; any patients with postural issues currently undergoing physiotherapy, chiropractic or medical treatment; any patient taking prescription medication for Neuralgias; any patient taking any steroid or any narcotic analgesics for pain; any patient that has had previous Botox treatment within the past 12 months.

The following consideration are given to patient enrollment. 1. Presence of any severe medical or psychological condition that, in the opinion of the Investigator, would compromise the participant's safe participation; 2. Immunocompromised by other types of viral infections or has a history of any other hepatitis form e.g. types A, C, D, E; 3. Underlying diseases or other dermatologic conditions that require the use of interfering topical or systemic therapy or that might interfere with study assessments such as, but not limited to, atopic dermatitis, perioral dermatitis, sebhorriac dermatitis, rosacea or serus lupus erythematosis. This includes clinically significant abnormal findings, uncontrolled or serious disease, or any medical or surgical condition, that may either interfere with the interpretation of the clinical trial results, and/or put the subject at significant risk (according to Investigator's judgment) if he/she participates in the clinical trial; 4. The subject has received, applied or taken some specified treatments within the specified timeframe prior to the Baseline visit; 5. The subject is unwilling to refrain from use of prohibited medication during the Clinical Trial; 6. Use of hormonal contraceptives solely for control of acne; 7. Presence of any condition (medical, psychological, social, or geographical), actual or anticipated, that the Investigator feels would restrict or limit the participant's successful participation for the duration of the study. 8. Receipt of any investigational treatment (medical device or drug) within 30 days prior to baseline visit; 9. Previous participation in a Ag4O4 or silver medical device study; and 10. Known allergy to silver or Ag4O4 nano particles.

A party (Director) will be placed in charge of the logistical coordination of the different study committees. An Executive Committee will be established, composed of Investigator/Academic Members from participating countries and Sponsor Representatives. This Committee will be led by the Principal Investigator for this trial, who will provide scientific and strategic direction for the trial and will have overall responsibility for its execution. An Operations Committee will be established, which will be responsible for ensuring that study execution and management are of the highest quality. This Committee will be composed of the Chairman and co-Chairmen of the Executive Committee, as well as the Principal Investigator and nonvoting Sponsor Representatives. It will determine its own guidelines and approve the criteria and guidelines of the other Committees prior to commencement of the study. The Operations Committee will convene regularly (at least every month) to discuss and report on the progress of the study. A Clinical Events Committee (CEC) will be established, composed of multidisciplinary academic members. This Committee will be responsible for validating and classifying, in a blinded fashion, all the primary efficacy outcome events reported by the Investigators. A Data Monitoring Committee (DMC) will be established, composed of Academic Members who are not otherwise participating in the trial. This Committee, led by its Chairman, will be responsible for the monitoring of patient safety, and it will be supported by an external DMC-associated statistician. The DMC can request any analysis during the course of the study, on either a blinded or un-blinded basis. The independent DMC-associated statistician will perform the planned analyses as well as the other analyses requested by the DMC, independently from the Sponsor. This independent statistician will be provided with the randomization code list, as well as with regular database transfers. He/she will prepare pro-forma tables, listings, and a report for submission to the DMC. Safety data will include serious adverse events (SAEs), outcome events, local laboratory values, plus other adverse events (AEs) as requested by the DMC. Demography, treatment and trial status data will be presented as requested by the DMC. The report will be based on current data, whether clean or not, and whether adjudicated or not. Although efficacy data will be provided, DMC review of these data does not constitute a formal interim analysis of efficacy, and any analyses of these data will not, in and of themselves, be used for stopping the trial.

Investigational Drug Description—Presentation: Clear, aqueous liquid, for intramuscular injection administration only, containing either: 100 units Botox diluted with 1.0 ml of 10 ppm (pH of 7.2 adjusted) AGRX® wound wash solution; or 100 units Botox diluted with 1.0 ml of 0.9% sterile saline solution. Modalities of administration: In a normal sterile fashion and using Allergan's BOTOX® clinical instructions for preparing the product for injection or by substituting the saline for AGRX® wound wash solution; the product is the drawn up into using B&D insulin syringe 1 mL for 100 units. A 30 G ultra fine needle, 8 mm length, is used to administer the drug to the body of the masseter muscle through dermal penetration. 30 units of the treatment solution is injected bilaterally into the body of the right and left masseter muscle in a triangular pattern. The injections are to be made as follows: 10 units of solution injected superiorly into the body of the masseter muscle below its insertion point on the inferior surface of the zygomatic arch; 10 units of solution injected inferior and anterior into the body of the masseter muscle above its insertion point into the lateral border of the mandible; 10 units into the body of the masseter muscle posteriorly and superiorly to where it inserts into the lateral aspect of the angle of mandible. A Total 60 units per patient shall be administered during treatment phase.

Dosage according to study group: Arm 1: 40 participants receiving bilateral masseter muscle injections of BOTOX® and AGRX® combination treatment in the amount of 30 units per masseter (per side) with approximately 0.3 ml of solution for a total of 60 units of BOTOX® or each participant. Arm 2: 40 participants receiving unilateral masseter muscle injection of BOTOX® and receiving unilateral masseter muscle injection AGRX® combination treatment in the amount of 30 units in one masseter with approximately 0.3 ml of AGRX® wound wash solution. The remaining untreated masseter receiving a combination of BOTOX® with approximately 0.3 ml of 0.9% sterile saline solution for a total of 60 units of BOTOX® for each participant. Arm 3: 40 participants receiving bilateral masseter muscle injections of 30 units of BOTOX® with approximately 0.3 ml of 0.9% sterile saline solution per masseter for a total of 60 units of BOTOX® for each participant.

Description of Blinding Methods. The two types of solution developed (BOTOX® and AGRX® combination treatment 10 ppm Ag Solution and BOTOX® with 0.9% sterile saline solution control) are indistinguishable (identical in size, shape, color, and appearance), and are assembled by a contract pharmacy into ready to use, pre-filled 10 ml vials. Identification will be controlled by lot number/assembly date and QR code on permanent labels on both vial bottle and box packaging.

Method of Assigning Participants to Treatment Group. The Director will provide a clinical trial website center which will allocate treatment group assignment based on a pre-specified randomization list, generated by the Director, using the study center(s) as stratification parameter. A list of treatment kit numbers for each treatment group is generated centrally by a selected Pharmacy and the treatment kits are prepared in accordance with this list. Numbers will not be reused regardless of the status of the use of the corresponding study medical device.

After the participant understands the trail and the commitment, signs the informed consent, and after eligibility is documented based on inclusion/exclusion criteria, the Principal Investigator will email the information form (showing subject ID number only) to the selected Pharmacy to receive the number for that treatment kit and only after the subject number is allocated to the patient. Participants will be considered randomized as soon as the first allocation of treatment kit number is given as documented by the selected Pharmacy.

All participants who are allocated a treatment kit number (i.e., randomized) by the selected Pharmacy irrevocably in the study, whether or not they are subsequently found to be eligible or actually receive the allocated treatment, and they should be followed until the End of Study visit or death, whichever comes first.

The first study intake (treatment) should take place as soon as possible after randomization (on the same day), under medical supervision. If participants temporarily discontinue study, they should contact the PI and coordinate a plan continue medical follow up for the next 18 months.

Packaging and Labeling. AGRX® 10 ppm Solution and matching placebo will be packaged in one (1) 10 mL vial. Each box will contain one (1), ten (10) mL vial and will be labeled with a treatment number (in addition to protocol number, expiry date, packaging number, and all the necessary regulatory statements required for participating in the study). One (1), ten (10) mL vial will be placed in a kit box, which will contain a single dose supply of treatment. One kit boxes will be placed in a partial shipment unit (PSU) box with a set of decoding envelopes, for the purpose of unblinding the treatment. Each kit box will bear a unique treatment number corresponding to the treatment number on each of the ten (10) mL vials. All kit box labels will be in English will meet regulatory requirements necessary.

A patient who completes the protocol as defined will have one (1) unique treatment kit numbers, created from randomization.

Storage Conditions. All investigational medical device supplies in the study will be stored in a secure, safe place, under the responsibility of a named organization, and shall be stored at the location until time of shipment. BOTOX Storage: Unopened vials of BOTOX should be stored in a refrigerator (2° to 8° C.) for up to 36 months. Do not use after the expiration date on the vial. Administer BOTOX within 24 hours of reconstitution; during this period reconstituted BOTOX should be stored in a refrigerator (2° to 8° C.). Reconstituted BOTOX should be clear, colorless, and free of particulate matter. AGRX® Storage: Stored at room temperature, in a dry safe place and in complete single dose cartons. The vial is only to be removed at the time of combining with BOTOX. After combining with BOTOX the storage and handling should follow the BOTOX storage and handling instructions.

Access to the Randomization Code During the Study. The Investigator will be supplied with one decoding envelope for each treatment kit number. It is the responsibility of the Investigator to ensure that these decoding envelopes are safely stored, but are readily available to the relevant staff. Additional unblinding materials (envelopes) will be available and are to be kept in a safe place at CRU level (or subcontractor, if any) throughout the clinical trial. The Sponsor will retrieve all envelopes, whether opened or sealed, on study completion.

In case of a Serious Adverse Event, the code should be broken only in exceptional circumstances when knowledge of the Investigational Product is essential for treating the patient.

In case the physician at the investigational site believes unblinding is needed, he/she must first contact the Medical Advisor for further direction. All calls will be documented as appropriate to include date and time of the call, name of the Medical Advisor, name, qualification, and address of the physician contacting the Medical Advisor, patient ID, documentation of the request, and decision for unblinding or not. If possible, a contact should be initiated with the Monitoring Team before unblinding. In case the decision to unblind is made, the Investigator must document it with the date, time of day, and reason for unblinding, and report this information in the appropriate page of the CRF and source document. In addition, the CTW (24-hour unblinding service) must be notified of this decision. Note that when documenting the reason for unblinding, the Investigator must not provide any detail regarding the nature of the Investigational Product. The Investigator should not divulge medication detail to any Sponsor staff member, Sponsor's representative, or to any Study Committee members until database closure. Furthermore, when completing forms (e.g., AE, SAE), the study treatment should not be disclosed on the forms. The unblinding envelopes will be sealed again and stored at the site level until the end of the study (envelopes opened by the CRU or a subcontractor must also be sealed again).

The Investigator or other personnel allowed to store and dispense Investigational Product (IP) will be responsible for ensuring that the IP used in the study is securely maintained as specified by the Sponsor and in accordance with the applicable regulatory requirements. All IP shall be dispensed in accordance with the Investigator's prescription and it is the Investigator's responsibility to ensure that an accurate record of IP issued and returned is maintained. Any quality issue noticed with the receipt or use of an IP (deficient IP in condition, appearance, pertaining documentation, labeling, expiry date, etc.) should be promptly reported to the Sponsor, who will initiate a complaint procedure. Under no circumstances will the Investigator supply IP to a third party, allow IP to be used other than as directed by this Clinical Trial Protocol, or dispose of IP in any other manner.

All partially used or unused treatments will be retrieved by the Sponsor. A detailed treatment log of the returned IP will be established with the Investigator (or the pharmacist) and countersigned by the Investigator and the Monitoring Team. The Investigator will not destroy unused IP unless the Sponsor provides written authorization to the contrary. A potential defect in the quality of IP may be subject to initiation by the Sponsor of a recall procedure. In this case, the Investigator will be responsible for promptly ad-wash any request made by the Sponsor, in order to recall IP and eliminate potential hazards.

The only concomitant treatment that may be undertaken shall be regular dental care pro re nata. Specifically prohibited concomitant treatment includes: Prescription drug or OTC indicated for hepatitis B treatment. However, any medical devices other than those listed above are allowed, and should be administered, as necessary for the treatment of the patient, when possible with a stable dose, at the discretion of the Investigator. All treatment with these medical devices should be recorded on the appropriate CRF.

Patients who are non-compliant with their pre-scheduled appointments and fail to keep consecutive appointments will, at the discretion of the Sponsor and the CPI, be removed from the study. Patients who routinely fail to follow the prescribed post-operative instructions may, at the discretion of the Sponsor and the CPI, be removed from the study.

After initial contact and pre-qualification through enrollment website (2,048 bit encryption) the participant shall be provided with an appointment for enrollment. All Patients (whether new or existing patients of the dental clinic) shall provide a full medical and dental history. All patients shall be given a complete dental exam and any necessary diagnostic tests shall be performed so that a dental diagnosis can be established by the participating investigator. A diagnosis for either clenching, grinding, nocturnal bruxism or TMJD must be first pre-enrollment criterion for their participation. The determination as to whether a patient is a good candidate for this trial shall then be left to the sole discretion of the chief clinical health care provider at the location of the trial.

Study participants will be recruited from email list recruitment, clinics, and diagnostic centers, under the responsibility of the chief clinical health care provider at the location of the trial. Patients may be enrolled at more than one dental clinics. Prior to initiation of the recruitment phase, the participating Investigator will identify a pool of potential study subjects. Each participating dental clinic will identify potentially eligible participants in advance, by either reviewing past medical records and diagnosis or treatment of a clenching or grinding disorder, nocturnal bruxism or TMJD whether professionally diagnosed or personal opinion of condition.

Each patient will undergo a baseline visit. The patient will receive complete information about the study in writing and orally if they choose. Written informed consent must be obtained from the patient prior to any study-specific procedures and prior to randomization. Compliance with inclusion criteria and exclusion criteria will be checked on the basis of information collected, and recorded in the CRF. Key baseline patient characteristics obtained at the randomization visit will be recorded in the CRF, including demographics, height, weight, relevant past medical and surgical history, including neurological and psychiatric history, and abnormalities noted on physical exam, including any past oral surgery and dental treatments. Medical history, physical examination, laboratory, or instrumental results confirming inclusion and absence of exclusion criteria will be maintained in the participant's file. Prior to Botox injections each patient will undergo Baseline EMG tracings using a K7 EMG Pre Amp and software by Myotronics, Inc. EMG biometric data will be collected on the patient's masseter muscles both at physiologic rest and during maximum clenching. This biometric date will later be compared to ongoing EMG tracings to help determine comparative endpoint efficacy.

Once all inclusion/exclusion criteria are fulfilled, the patient becomes eligible for randomization and inclusion into the treatment period. Participants will be counseled to follow a healthy diet, to increase their water consumption and to stop smoking, if they are smokers.

Description by Type of Visit. Baseline enrollment form completed and submitted online (secure site), informed consent signed and submitted. Initial parameter acceptance in 24 hours of initial enrollment form submission. Sent via email to potential participant. Telemedicine diagnosis link and payment provided to potential participant. Diagnosis form submitted, aqueous kit dispensed and sent to participant. Participant followed via App submission data for safety and compliancy two time per week during the Clinical Trial period during the treatment period of one month. Follow up call, email and follow up summary completed by dermatologist at the end of the one month treatment period with written results. Three (3) month participant courtesy email to confirm safety and answer any questions. There is no strict timing for the phone calls. In any case, it is better to call the patient after a delay, than to not call them at all (even in this case, the phone call record page of the CRF should be completed). The patient visit schedules will be given by the CTW as soon as the participant is randomized, so as the Investigator can plan in advance all the necessary appointments with the participant.

Definition of Source Data. All the data collected in the CRF come from source documents that are part of the patient dossier. Copies of some of those source documents will be collected after anonymization, in order to support documentation of outcome events eligible for validation by the Clinical Events Committee, i.e.: (a) for any of those events: a copy of the Hospital Discharge Summary and a clinical description of the event by the Investigator; (b) for any death: a copy of the death certificate (if applicable and available), autopsy report (if available), 12-lead ECGs (all, including baseline), other relevant reports, and witness description of the death; (c) for any sudden death: a copy of recent Holter reports (if available) and cardiology notes; (d) for MI: a copy of the ECG tracings selected from serial ECG and documenting Q-wave MI or non Q-wave MI, biochemical reports (cardiac markers+laboratory reference values) selected from serial tests (e.g., peak values) relevant to the diagnosis of MI or re-MI, autopsy report (if available) or other relevant reports (coronary angiography, echocardiography); (e) for stroke: CT-scan/MRI report and copy of the films, autopsy report (if available) or other relevant reports (angiography, Doppler sonography).

The primary goal of this trial is to illustrate a significant increase in the length of time the masseter muscle remains relaxed when injected with Botox and AGXR (as compared to those muscles injected with Botox with saline). For the purposes of this trial a significant increase is defined as a 25% or greater increase in the time the masseter muscle remains relaxed in at least 75% of the participants. This increased relaxation time will be measured using objective biometric data generated by K7 EMG equipment from Myotronics Inc., and will determined by measuring a prolonged decrease in the EMG data during maximum clench (decreased muscle spasticity) compared to the previous baseline data for that same muscle (prior to injection).

The following efficacy criteria will be used for the trial. Primary: Since the primary goal of this trial is illustrate a significant increase in the length of time the masseter muscle remains relaxed when injected with Botox and AGXR the most accurate, analytical and objective method of achieving this is via the use of quantitative EMG biometric data. Increased relaxation times will be quantified by providing real time biometric data that illustrates in a graph style format (expressed in microvolts per second) a decrease in maximum clenching capability when compared to pre injection baseline data. Once these muscle contraction values begin to rise to pre injection levels the efficacy criteria for return to normal values will be met. By comparing these values for both diluents the investigators will be able to quantitatively determine which Botox effect lasts longer and by how much. Secondary: A dental exam will be conducted on all patients and on all masseter muscles injected with Botox. Range of motion, maximum clenching force and speed of jaw closure will be evaluated and noted but this type of clinical assessment of extended muscle relaxation will be nothing more than a subjective assessment.

The following Primary Criterion will be utilized. Composite success rate: Safety—no issues or reported adverse conditions.

Clinical Assessment Methods: Primary: EMG monitoring of Masseter muscles injected with BOTOX using Myotronics K7 EMG Pre-Amp and Computer Software Program. The EMG electrode system that will be utilized as part of this clinical protocol to determine the clinical endpoint of the Botox injections were specifically designed as trans dermal electrodes (duotrodes) with a silver chloride adhesive backing. These dermal electrodes are connected via are connected via dual wire leads to a pre amp which is connected to a computer software program that measures muscle activity in the masseter muscles bilaterally in real time and in one second increments. The duotrode pads are placed over top of the body of both right and left masseter muscles with the long axis of the electrode parallel to the long axis of the muscle fibres. The adhesive backing of these duotrodes is to make intimate contact with the overlying skin. The dual wire leads of each duotrode are attached via alligator snaps on one end and quick connect plugs into the K7 Myotronics EMG pre amp on the other end. The preamp is then connected to a laptop computer containing the K7 diagnostic software and when the EMG program is turned on it measures (in real time) the Masseter muscle activity both at rest and while clenching in micro-volts per second. These EMG electrodes wired to the K7 Pre Amp and computer software program allows the clinician to analytically and objectively determine whether or not the Botox injected masseter muscle is still in a state of spasticity. This is preferable to trying to subjectively determine the same outcome. In the case of this particular clinical trial it allows comparison of right and left Masseter muscle activity and whether or not the Botox effect on the muscle has worn off. This is done by comparing the subsequent EMG readings to the original baseline maximum clench values. When these EMG values start returning to the pre-injection values will have reached a definitive end point. At this time we will be able to analytically compare the definitive end point values of the two separate diluents and make objective assessments as to whether or not the AGRX diluent is able to significantly increase the length of time of muscle relaxation.

Clinical Assessment Methods: Secondary: Photos of treatment areas over the course of the study during their regularly scheduled appointments.

Clinical Assessment Methods: Tertiary: Participant survey completed at time of photo submissions.

The primary efficacy end point of this study is defined by a return of the masseter muscle to pre injection baseline levels of maximum clenching force expressed in micro volts per second using biometric digital data from a Myotronics K7 EMG pre Amp. These readings will vary from patient to patient based on their baseline readings and it is anticipated by this study that those masseter muscles injected with Botox and saline diluent will return to pre injection baseline levels of maximum clenching force sooner than those masseter muscles injected with Botox and AGRX.

All of the U.S. patents, U.S. patent application publications, U.S. patent applications, foreign patents, foreign patent applications and non-patent publications referred to in this specification and/or listed in the Application Data Sheet are incorporated herein by reference, in their entirety.

From the foregoing it will be appreciated that, although specific embodiments of the invention have been described herein for purposes of illustration, various modifications may be made without deviating from the spirit and scope of the invention. Accordingly, the invention is not limited except as by the appended claims.

What is claimed is:

1. A method of treating wrinkles, comprising administering a composition by injection to a subject in need thereof, the composition comprising botulinum toxin (BTX), colloidal silver particles, and at least one of water, saline and buffer, the composition comprising from 10±5 ppm to 30±5 ppm colloidal silver particles for every 100 units of BTX suspended in the water, and wherein the colloidal silver particles are in the form of a stable and colorless colloidal suspension of silver particles having an interior of metallic silver and an exterior surface of ionic silver oxide, wherein at least 75% of the silver particles have diameters between 0.005 micrometers and 0.015 micrometers, and storing the composition for a period of from 2 weeks to 4 months after preparation of the composition, prior to the administering of the composition to the subject; and wherein the administration is effective to treat static or functional wrinkles for a period of 7.5 months to 10 months.

2. A method of treating wrinkles, comprising administering a composition by injection to a subject in need thereof, the composition comprising botulinum toxin (BTX), colloidal silver particles, and water, the composition comprising an amount of from 10±5 ppm to 30±5 ppm colloidal silver particles for every 100 units of BTX suspended in the water where the amount is effective to treat static or functional wrinkles for a period of 7.5 months to 10 months, and wherein the colloidal silver particles are in the form of a stable and colorless colloidal suspension of silver particles having an interior of metallic silver and an exterior surface of ionic silver oxide, wherein at least 75% of the silver particles have diameters between 0.005 micrometers and 0.015 micrometers.

3. The method of claim 2 wherein the composition comprises about 30 ppm colloidal silver.

4. The method of claim 2 wherein the composition comprises 30 ppm colloidal silver.

* * * * *